United States Patent [19]

Funaki et al.

[11] 4,435,203
[45] Mar. 6, 1984

[54] OPTICAL ISOMER OF TRIAZOLYLPENTENOLS, AND THEIR PRODUCTION AND USE AS FUNGICIDE, HERBICIDE AND/OR PLANT GROWTH REGULANT

[75] Inventors: Yuji Funaki, Toyonaka; Yukio Yoneyoshi, Otsu; Yukio Ishiguri; Kazuo Izumi, both of Takarazuka, all of Japan

[73] Assignee: Sumitomo Chemical Company, Limited, Osaka, Japan

[21] Appl. No.: 328,191

[22] Filed: Dec. 7, 1981

[30] Foreign Application Priority Data

Dec. 15, 1980 [JP] Japan ................... 55-177704
Dec. 22, 1980 [JP] Japan ................... 55-182407

[51] Int. Cl.³ .................. A01N 43/64; C07D 249/08
[52] U.S. Cl. .......................... 71/76; 71/92; 424/269; 542/458
[58] Field of Search ............ 542/458; 424/269; 71/76, 92

[56] References Cited

U.S. PATENT DOCUMENTS 4,203,995 5/1980 Funaki et al. ............... 548/262
4,331,675 5/1982 Regel et al. ............... 542/458

FOREIGN PATENT DOCUMENTS 4918 10/1979 European Pat. Off. .
2743767 4/1979 Fed. Rep. of Germany ...... 424/269
2920437 11/1980 Fed. Rep. of Germany ...... 548/262
55-105672 8/1980 Japan .
2046260 11/1980 United Kingdom ............... 548/262

OTHER PUBLICATIONS

Karrer, Organic Chemistry, (Second English Edition, N.Y., 1946), pp. 93–97.

Primary Examiner—Alton D. Rollins
Attorney, Agent, or Firm—Stevens, Davis, Miller & Mosher

[57] ABSTRACT

This invention relates to a triazolyl alcohol derivative having an optical activity of (−) or (+) and represented by the general formula (I),

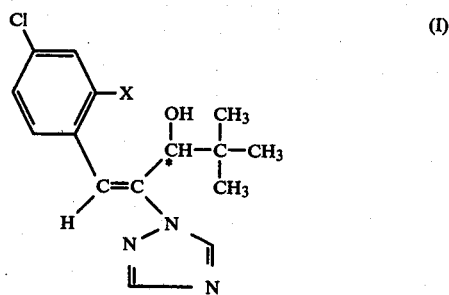

wherein X represents a hydrogen atom or a chlorine atom and the asterisk indicates an asymmetric carbon atom, a process for preparing same, and a fungicide containing same as active ingredient.

10 Claims, No Drawings

OPTICAL ISOMER OF TRIAZOLYLPENTENOLS, AND THEIR PRODUCTION AND USE AS FUNGICIDE, HERBICIDE AND/OR PLANT GROWTH REGULANT

This invention relates to an optically active triazolyl alcohol derivative having an optical activity of either (−) or (+), and which may be represented by the general formula (I),

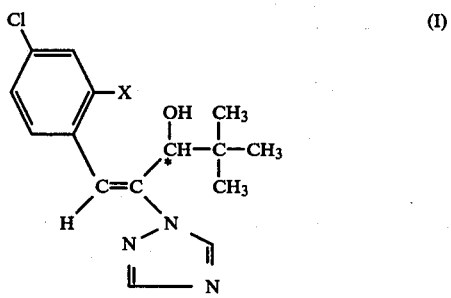

wherein X represents a hydrogen atom or a chlorine atom and the asterisk indicates an asymmetric carbon atom, a process for preparing same, and a fungicide containing same as active ingredient.

The racemic triazolyl alcohol derivatives and their excellent fungicidal, plant growth regulatory, and herbicidal activities have already been described in Japanese Patent Application "Kokai" (Laid-open) No. 124,771/1980 and Japanese Patent Application No. 100,547/1980.

Triazolyl alcohol derivatives represented by the general formula (I) have optical isomers due to the asymmetric carbon atom (*C). The triazolyl alcohol derivative (I) having an optical activity of (−), as above referred to, is an optical isomer which shows an optical rotation of (−), as measured in chloroform with sodium D line, and is hereinafter referred to as (−)-triazolyl alcohol derivative. On the other hand, another isomer which shows an optical rotation of (+) is hereinafter referred to as (+)-triazolyl alcohol derivative. Salts of the triazolyl alcohol derivatives are also included in the scope of this invention. These salts are salts with the plant-physiologically tolerable acids. Examples of such acids include hydrogen halides such as hydrobromic acid, hydrochloric acid and hydroiodic acid; carboxylic acids such as acetic acid, trichloroacetic acid, maleic acid and succinic acid; sulfonic acids such as p-toluenesulfonic acid and methanesulfonic acid; nitric acid, sulfuric acid, and phosphoric acid. These salts are obtained in a customary manner.

The present inventors examined in detail the usefulness of (−)- or (+)-triazolyl alcohol derivatives (I) obtained by the process of this invention. Upon comparison of (−)-, (+)- and racemic triazolyl alcohol derivatives with one another, it was found that the fungicidal activity falls in the order: (−)-triazolyl alcohol derivative > racemic triazolyl alcohol derivative > (+)-triazolyl alcohol derivative, whilst the plant growth regulatory activity and the herbicidal activity are in the order: (+)-triazolyl alcohol derivative > racemic triazolylalcohol derivative > (−)-triazolyl alcohol derivative. In short, the present inventors have discovered an entirely new fact that a (−)-triazolyl alcohol derivative exhibits an excellent fungicidal activity, while a (+)-triazolyl alcohol derivative exhibits an excellent plant growth regulatory activity and herbicidal activity.

The present invention contributes much to the plant disease control or to the cultivation or more resistive plant in the fields of agriculture and horticulture. For instance, application of a more active chemical is connected to adequate application of a smaller amount of the chemical, which leads to the improvement in economics of the processes of manufacture, transportation and field application and to the expectation of minimizing the environmental pollution as well as the improvement in safety. In applying (−)-triazolyl alcohol derivatives as a fungicide, no harmful effect on the plant will be exhibited even if an excess of the compound has been applied by the misuse and, hence, it is safely used in controlling injurious plant diseases.

The plant diseases which can be effectively controlled by (−)-triazolyl alcohol derivatives include blast and sheath blight of rice plant; canker, blossom blight, powdery mildew, scab, fruit spot and alternaria leaf spot of apple; black spot, powdery mildew, rust and scab of Japanese pear; melanose, scab, anthracnose, common green mold and blue mold of mandarin orange; brown rot of peach; ripe rot, gray mold, powdery mildew and rust of grape; crown rust of oat; powdery mildew, scald, leaf stripe, loose smut, covered smut, snow blight and black rust of barley; brown rust, loose smut, stinking smut, speckled leaf blotch, glume blotch, yellow rust, stem rust and powdery mildew of wheat; powdery mildew, gray mold, gummy stem blight, sclerotinia rot and anthracnose of melons; leaf mold, powdery mildew and early blight of tomato; gray mold, verticillium wilt and powdery mildew of eggplant; powdery mildew of pimento; gray mold and powdery mildew of strawberry; brown spot and powdery mildew of tobacco; cerespora leaf spot of sugar beet; and leaf spot of peanut.

As stated above, the (+)-triazolyl alcohol derivatives can be utilized as plant growth regulators to regulate the growth of useful plants. For instance, they can be applied to keep the rice plant, wheat and barley, lawn grass, hedge plants and fruit trees from spindle growth and also to effect dwarfing of potted garden plants such as chrysanthemum, pansy, poinsettia, azalea, rhododendran and the like. In rice cropping and wheat or barley cropping, the lodging of rice, wheat or barley plant caused by excessive application of fertilizers or by the gale often presents an important problem. By applying a (+)-triazolyl alcohol derivative to rice, wheat or barley in a proper stage of growth, the spindling can be suppressed so that the plant height may be suitably controlled to keep effectively the plant from lodging. In the cultivation of chrysanthemum in pot, application of the compound results in a reduction in the stem length without injurious effect on the flower, thus improving the commercial value of the plant.

Further, the (+)-triazolyl alcohol derivatives exhibit a strong herbicidal activity against gramineous weeds such as barnyard millet, large crabgrass and green foxtail; cyperaceous weeds such as purple nutsedge; broad-leaved weeds in upland field such as green amaranth, fat hen, common purslane and common chickweed; annual and perennial weeds in paddy field such as barnyardgrass, monochoria, spike-flowered rotala, *Dapatrium junceum*, bulrush and slender spikerush.

When applied to an upland field, the (+)-triazolyl alcohol derivatives exhibit a strong activity against principal weeds and are effective for the preemergence treatment of soil as well as for the foliage treatment in an early stage of growth. The compounds have tremendous advantages in that they have no harmful effect on principal crops such as rice, soybean, cotton, corn, peanut, sunflower and sugar beet and can be safely used also for the vegetables such as lettuce, radish and tomato. The compounds, therefore, are useful for the weeding of a variety of grain fields, vegetable garden, orchard, lawn, pasture, tea field, mulberry field, rubber plantation, forest land, non-cultivation field, etc. It was found, moreover, that the compounds are highly non-toxic to mammals and fishes and are substantially harmless to agriculturally useful crops.

The methods for preparing the (+)- or (−)-triazolyl alcohol derivatives include those used in preparing conventional optically active substances such as the asymmetric reduction and the resolution of the diastereomer obtained from a racemate and an optically active reactive compound. These methods are described below in detail.

(1) PREPARATION BY ASYMMETRIC REDUCTION

The racemate of the present compound is obtained by reducing a ketone compound represented by the general formula (II) with a metal-hydrogen complex such as lithium aluminum hydride ($LiAlH_4$) or sodium borohydride ($NaBH_4$) [Japanese Patent Publication "Kokai" (Laid-open) No. 124,771/1980].

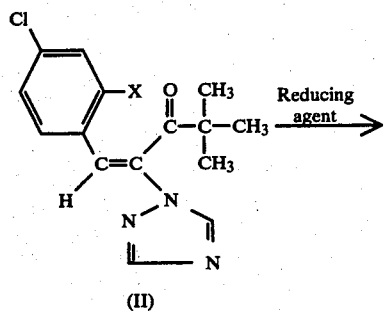

(II)

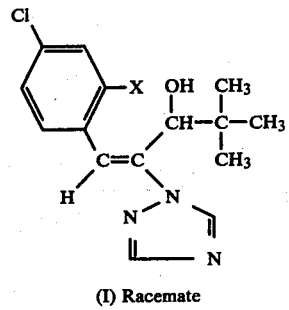

(I) Racemate wherein X represents a hydrogen or chlorine atom. The asymmetric reduction is commonly conducted by utilizing the enantioselective reaction which takes place when a ketone compound (II) is reduced with a chiral metal-hydrogen complex. A few of such procedures are described below.

(a) It is a general practice to use as the chiral metal-hydrogen complex a reducing agent of the chiral modified lithium aluminum hydride type formed by the partial decomposition of lithium aluminum hydride with an optically active alcohol [Literature: Tetrahedron Letters, Vol. 29, 913 (1973); Bull. Soc. Chim. Fr., 1968, 3795; J. Org. Chem., 38 (10), 1973; Tetrahedron Letters, Vol. 36, 3165 (1976)].

Among examples of the optically active alcohols used in this invention as asymmetric source, may be cited (+)- or (−)-menthol, (+)- or (−)-borneol, (+)- or (−)-N-methylephedrine, and (+)- or (−)-2-N,N-dimethylamino-1-phenylethanol. It is of course possible to use either of the optically active forms of other optically active alcohols including alkaloids, carbohydrates and amino alcohols such as, for example, quinine, cis-Myrtanol, 2-N-benzyl-N-methylamino-1-phenylethanol and 4-dimethylamino-3-methyl-1,2-diphenyl-2-butanol. The formation of a chiral modified lithium aluminum hydride reducing agent using an optically active alcohol as asymmetric source can be effected by adding 1 to 3 equivalent ratio of the optically active alcohol to one equivalent ratio of lithium aluminum hydride suspended in a suitable solvent. It is a general practice to use as the solvent an ether such as diethyl ether, tetrahydrofuran or dioxane, though an aromatic hydrocarbon such as benzene or toluene or an aliphatic hydrocarbon such as n-hexane or n-pentane may also be used.

(b) It is sometimes advantageous to use as the chiral metal-hydrogen complex a chiral modified lithium aluminum hydride reducing agent formed by the reaction of one equivalent ratio of an optically active alcohol, 2 equivalent ratio of a N-substituted aniline represented by the general formula (III),

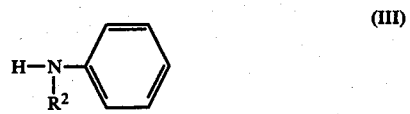

(III)

wherein $R^2$ is a lower alkyl group or a phenyl group, and one equivalent ratio of lithium aluminum hydride[-literature:Tetrahedron Letters, Vol. 21, 2753 (1980)]. The optically active alcohol used as asymmetric source in this invention is exemplified by either of the optically active forms of an optically active amino alcohol such as, for example, (+)- or (−)-N-methylephedrine or (+)- or (−)-2-N,N-dimethylamino-1-phenylethanol. As to the N-substituted aniline, a desirable result is obtained by use of a lower alkyl-substituted aniline such as N-methylaniline or N-ethylaniline, or diphenylamine. The preparation of such a chiral modified lithium aluminum hydride reducing agent can be achieved by suspending one equivalent ratio of lithium aluminum hydride ($LiAlH_4$) in a suitable solvent and admixing with one equivalent ratio of an optically active alcohol followed by 2 equivalent ratio of a N-substituted aniline. The solvent described above in (a) can be used likewise.

The asymmetric reduction is conducted by adding a ketone compound (II) dissolved in a suitable solvent to the chiral modified lithium aluminum hydride prepared as in (a) or (b) described above. The solvent is the same as described in (a). The reaction temperature is preferably 0° C. or below, though a temperature between −80° C. and the boiling point of the solvent can be used. After completion of the reaction, the complex compound is decomposed by the addition of a dilute aqueous acidic solution and the reaction mixture is purified by extraction, silica gel column chromatography or recrystallization to obtain the intended product.

(2) PREPARATION BY RESOLUTION OF DIASTEREOMERS

A method for resolving optical isomers by use of diastereomer esters formed from a racemic alcohol compound and an optically active reactive compound has been known (literature: Org. Reaction, Vol. 2, 380). A diastereomeric ester mixture (IV) is obtained by allowing a racemate of triazolyl alcohol compound (I) to react with a reactive derivative of optically active carboxylic acid in the presence of a base. A (−)- or (+)-triazolyl alcohol derivative (I) is obtained by resolving said diastereomeric ester mixture by chromatography or fractional crystallization into (+)-triazolyl alcohol ester and (−)-triazolyl alcohol ester, and decomposing said esters.

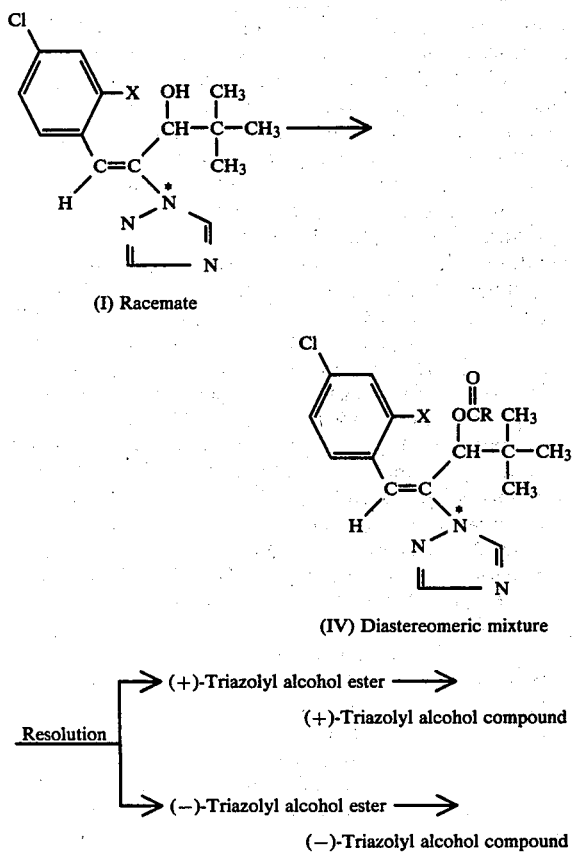

(In the above formulas, X and the asterisk are as defined above.)

As examples of the optically active carboxylic acids for use in the esterification of racemate of a triazolyl alcohol (I), there are (−)-menthoxyacetic acid, (+)- or (−)-N-trifluoroacetylproline, (+)-camphoric acid, (+)- or (−)-mandelic acid, (+)- or (−)-2-phenylpropionic acid, (+)- or (−)-2-isopropyl-4′-chlorophenylacetic acid, (+)- or (−)-α-methoxy-α-trifluoromethylphenylacetic acid, (+)- or (−)-cis-chrysanthemic acid, and (+)- or (−)-transchrysanthemic acid. The reactive derivatives of these optically active carboxylic acids include acid halides and acid anhydrides. Generally, the optically active carboxylic acid is converted into an acid halide in a customary manner and allowed to react with the racemate of a triazolyl alcohol (I) to effect esterification. The reaction is conducted in a common inert solvent (e.g., acetone, acetonitrile, tetrahydrofuran, ethyl acetate, benzene, toluene, dichloromethane, chloroform and carbon tetrachloride) and in the presence of a dehydrohalogenation agent (e.g., triethylamine, N,N-dimethylaniline and pyridine). Generally, 1 to 5 moles of an acyl halide and a dehydrohalogenation agent are used for one mole of the triazolyl alcohol racemate (I). Pyridine behaves also as a solvent when used in excess. The reaction temperature is in the range of from room temperature to the boiling point of the solvent. It is of course possible to prepare the diastereomeric ester by using the anhydride of an optically active carboxylic acid.

When the diastereomeric mixture of a triazolyl alcohol ester (V) obtained as described above is crystallizable, it is resolved by repeated fractional crystallization, while if it is in oily form, the resolution is effected by column chromatography or high-speed liquid chromatography. The (−)- or (+)-triazolyl alcohol ester thus formed is decomposed in the presence of a base such as sodium hydroxide or potassium hydroxide in a suitable solvent such as water or an aqueous organic solvent (ethanol or methanol is generally used) to obtain a (−)- or (+)-triazolyl alcohol derivative (I).

In the field application of the compounds of this invention obtained as described above, they may be used either alone without the addition of other ingredients or in mixtures with a carrier to make them more convenient for use as a fungicide or a herbicide and a plant growth regulator. Examples of the usual preparation forms include dust, wettable powder, oil spray, emulsion, tablet, granule, fine granule, aerosol and flowable. These preparations contain generally 0.1 to 95.0%, preferably 0.2 to 90.0% by weight of the active compound (including other active ingredients). A suitable application rate is 2 to 500 g/10 ares and a preferable concentration of the active ingredients for field application is 0.001 to 1.0%. However, the concentration may be suitably increased or decreased without sticking to the said range, because the application rate and the concentration depend on the type of preparation, application time of the year, method of application, site of application, plant disease to be controlled and the type of crop to be treated.

For the use as fungicide, the (−)-triazolyl alcohol derivative (I) can be mixed with other fungicides such as, for example, N-(3,5-dichlorophenyl)-1,2-dimethylcyclopropane-1,2-dicarboximide, S-n-butyl S-p-tert-butylbenzyldithiocarbonimidate, 0,0-dimethyl 0-(2,6-dichloro-4-methylphenyl)phosphorothioate, methyl 1-butylcarbamoyl-1H-benzimidazol-2-yl-carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylenebisdithiocarbamate, zinc dimethylthiocarbamate, manganese ethylenebisdithiocarbamate, bis(N,N-dimethylthiocarbamoyl)disulfide, tetrachloroisophthalonitrile, 8-hydroxyquinoline, dodecylguanidine acetate, 5,6-dihydro-2-methyl-1,4-oxathiine-3-carboxanilide, N′-dichlorofluoromethylthio-N,N-dimethyl-N′-phenylsulfamide, 1-(4-chlorophenoxy)-3,3-dimethyl-1-(1,2,4-triazol-1-yl)-2-butanone, 1,2-bis(3-methoxycarbonyl-2-thioureido)benzene, methyl N-(2,6-dimethylphenyl)-N-methoxyacetyl-2-methylglycinate, and aluminum ethylphosphite.

Further, the (−)-triazolyl alcohol derivative (I) can be used in combination with other herbicidal and plant growth regulatory agents. Such a mixture does not reduce the control effect of each active component and even a synergetic effect is expectable from the joint use. Examples of such agents include phenoxy-type herbicides such as 2,4-dichlorophenoxyacetic acid, 2-methyl-4-chlorophenoxybutyric acid, 2-methyl-4-chlorophenoxyacetic acid, esters and salts thereof; diphenyl ether-type herbicides such as 2,4-dichlorophenyl 4'-nitrophenyl ether, 2,4,6-trichlorophenyl 4'-nitrophenyl ether, 2-chloro-4-trifluoromethylphenyl 3'-ethoxy-4'-nitrophenyl ether, 2,4-dichlorophenyl 4'-nitro-3'-methoxyphenyl ether, and 2,4-dichlorophenyl 3'-methoxycarbonyl-4'-nitrophenyl ether; triazine-type herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, and 2-methylthio-4,6-bisisopropylamino-1,3,5-triazine; urea-type herbicides such as 3-(3,4-dichlorophenyl)-1,1-dimethylurea, 3-(3,4-dichlorophenyl)-1-methoxy-1-methylurea, 1-(α,α-dimethylbenzyl)-3-p-tolylurea, and 1-(2-benzothiazolyl)-1,3-dimethylurea; carbamate-type herbicides such as isopropyl N-(3-chlorophenyl)carbamate and methyl N-(3,4-dichlorophenyl)carbamate; thiolcarbamate-type herbicides such as S-(4-chlorobenzyl) N,N-diethylthiolcarbamate and S-ethyl N,N-hexamethylenethiolcarbamate; acid anilide-type herbicides such as 3,4-dichloropropionanilide, 2-chloro-N-methoxymethyl-2',6'-diethylacetanilide, 2-chloro-2',6'-diethyl-N-(butoxymethyl)acetanilide, 2-chloro-2',6'-diethyl-N-(n-propoxyethyl)acetanilide, and N-chloroacetyl-N-(2,6-diethylphenyl)glycine ethyl ester; uracil-type herbicides such as 5-bromo-3-sec-butyl-6-methyluracil and 3-cyclohexyl-5,6-trimethyleneuracil; pyridinium salt-type herbicides such as 1,1'-dimethyl-4,4'-bipyridinum chloride; phosphorus-type herbicides such as N-(phosphonomethyl)glycine, N,N-bis(phosphonomethyl)glycine, O-ethyl O-(2-nitro-5-methylphenyl) N-sec-butyl phosphoroamidothioate, S-(2-methyl-1-piperidylcarbonylmethyl) O,O-di-n-propyldithiophosphate, and S-(2-methyl-1-piperidylcarbonylmethyl) O,O-diphenyldithiophosphate; toluidine-type herbicides such as α,α,α-trifluoro-2,6-dinitro-N,N-dipropyl-p-toluidine; 5-tert-butyl-3-(2,4-dichloro-5-isopropoxyphenyl)-1,3,4-oxadiazolin-2-one, 3-isopropyl-(1H)-2,1,3-benzothiadiazin-(3H)-one-2,2-dioxide, α-(β-naphthoxy)propionanilide, 4-(2,4-dichlorobenzoyl)-1,3-dimethylpyrazol-5-yl p-toluenesulfonate, 3-methoxycarbonylamino)phenyl 3-methylphenylcarbamate, and 4-amino-3-methyl-6-phenyl-1,2,4-triazine.

For the uses as herbicide and plant growth regulator, the present compound can be mixed with other fungicides and insecticides, and even a synergetic effect is expectable from such a mixture. Examples of fungicides include N-(3,5-dichlorophenyl)-1,2-dimethylcyclopropane-1,2-dicarboximide, S-n-butyl S-p-tert-butylbenzyldithiocarbonimidate, O,O-dimethyl O-(2,6-dichloro-4-methylphenyl)phosphorothioate, methyl 1-butylcarbamoyl-1H-benzimidazol-2-yl-carbamate, N-trichloromethylthio-4-cyclohexene-1,2-dicarboximide, cis-N-(1,1,2,2-tetrachloroethylthio)-4-cyclohexene-1,2-dicarboximide, Polyoxin, streptomycin, zinc ethylenebisdithiocarbamate, zinc dimethylthiocarbamate, manganese ethylenebisdithiocarbamate, bis(N,N-dimethylthiocarbamoyl)disulfide, tetrachloroisophthalonitrile, 8-hydroxyquinoline, dodecylguanidine acetate, 5,6-dihydro-2-methyl-1,4-oxathiin-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis(3-methoxycarbonyl-2-thioureid)benzene, methyl N-(2,6-dimethylphenyl)-N-methoxyacetyl-2-methylglycinate, and aluminum ethylphosphite. Examples of the insecticides include organophosphorus insecticides such as O,O-dimethyl O-(4- nitro-3-methylphenyl)phosphorothioate, O-(4-cyanophenyl) O,O-dimethylphosphorothioate, O-(4-cyanophenyl) O-ethylphenylphosphonothioate, O,O-dimethyl S-(1-ethoxycarbamoylmethyl)phosphorodithioate, 2-methoxy-4H-1,3,2-benzodioxaphosphorin-2-sulfide, O,O-dimethyl S-(1-ethoxycarbonyl-1-phenylmethyl)phosphorodithioate, and pyrethroid insecticides such as α-cyano-3-phenoxybenzyl 2-(4-chlorophenyl)isovalerate, 3-phenoxybenzyl 2,2-dimethyl-3-(2,2-dichlorovinyl)cyclopropanecarboxylate, and α-cyano-3-phenoxybenzyl 2′,2′-dimethyl-3′-(2,2-dibromovinyl)-cyclopropanecarboxylate.

The invention is further illustrated below in detail with reference to Examples, Reference Examples, Test Examples and Formulation Examples.

EXAMPLE 1

Synthesis of (−)- and (+)-(E)-1-(4-chlorophenyl)-2-(1,2,4-triazol-1-yl)-4,4-dimethyl-1-penten-3-ol by resolution of diastereomeric ester:

A mixture of 4.3 g of (±)-(E)-1-(4-chlorophenyl)-2-(1,2,4-triazol-1-yl)-4,4-dimethyl-1-penten-3-ol and 8 g of (−)-menthoxyacetyl chloride was stirred in 50 cc of pyridine at 70° C. for 7 hours. The reaction mixture was poured into 200 cc of ice water and extracted with 400 cc of ethyl acetate. The organic layer was washed successively with 0.5 N hydrochloric acid, 200 cc of a saturated aqueous sodium hydrogencarbonate solution and 200 cc of ice-cooled water, then dried over anhydrous sodium sulfate, and concentrated in vacuo. The resulting oily crude substance was purified by silica gel column chromatography (150 g of silica gel; developing solvent; n-hexane/acetone=30:1) to obtain 7.4 g of (±)-[(E)-1-(4-chlorophenyl)-2-(1,2,4-triazol-1-yl)-4,4-dimethyl-1-penten-3-yl]-(−)-menthoxy acetate. Upon repetition of chromatography on another silica gel column (250 g of silica gel; developing solvent; n-hexane/benzene/acetone=20/20/1), there were obtained 2.6 g of (−)-[(E)-1-(4-chlorophenyl)-2-(1,2,4-triazol-1-yl)-4,4-dimethyl-1-penten-3-yl]-(−)-menthoxyacetate ($n_D^{25}$1.5265) as first eluate, 3 g of the diastereomeric ester mixture as second eluate, and 1.2 g of (+)-[(E)-1-(4-chlorophenyl)-2-(1,2,4-triazol-1-yl)-4,4-dimethyl-1-penten-3-yl]-(−)-menthoxyacetate ($n_D^{25}$1.5281) as final eluate.

A mixture of 2.6 g of (−)-[(E)-1-(4-chlorophenyl)-2-(1,2,4-triazol-1-yl)-4,4-dimethyl-1-penten-3-yl]-(−)-menthoxyacetate and 40 cc of a 95% aqueous ethanol solution containing 0.4 g of potassium hydroxide was stirred at 30° C. for one hour. The reaction mixture was poured into 200 cc of ice water and extracted with 300 cc of ethyl acetate. The organic layer was dried over anhydrous sodium sulfate and concentrated in vacuo. The resulting crude crystals were recrystallized from a carbon tetrachloride-n-hexane mixture to obtain 1.2 g of (−)-(E)-1-(4-chlorophenyl)-2-(1,2,4-triazol-1-yl)-4,4-dimethyl-1-penten-3-ol: $[\alpha]_D^{24}$−16.0 (c=1, CHCl$_3$); m.p. 170°-171° C. The NMR spectrum was the same as that of the racemate described in Reference Example 1.

Similarly, 1.2 g of (+)-[(E)-1-(4-chlorophenyl)-2-(1,2,4-triazol-1-yl)-4,4-dimethyl-1-penten-3-yl]-(−)-menthoxyacetate was treated with 20 cc of a 95% aqueous ethanol solution containing 0.2 g of potassium hydroxide and the resulting crude crystals were recrystallized from a carbon tetrachloride-n-hexane mixture to obtain 0.5 g of (+)-(E)-1-(4-chlorophenyl)-2-(1,2,4-triazol-1-yl)-4,4-dimethyl-1-penten-3-ol: $[\alpha]_D^{24}$+14.0 (c=1.0, CHCl$_3$); m.p. 169°-170° C.

EXAMPLE 2

Synthesis of (−)- and (+)-(E)-1-(2,4-dichlorophenyl)-2-(1,2,4-triazol-1-yl)-4,4-dimethyl-1-penten-3-ol by resolution of diastereomeric ester:

A mixture of 4 g of (±)-(E)-1-(2,4-dichlorophenyl)-2-(1,2,4-triazol-1-yl)-4,4-dimethyl-1-penten-3-ol and 8 g of (−)-menthoxyacetyl chloride was stirred in 50 cc of pyridine at 70° C. for 7 hours. The reaction mixture was treated in the same manner as in Example 1. The crude oily substance was purified by silica gel chromatography (150 g of silica gel; developing solvent: n-hexane/acetone=30:1) to obtain 5 g of (±)-[(E)-1-(2,4-dichlorophenyl)-2-(1,2,4-triazol-1-yl)-4,4-dimethyl-1-penten-3-yl]-(−)-menthoxy acetate. Upon repetition of chromatography on another silica gel column (250 g of silica gel; developing solvent: n-hexane/benzene/acetone=20/20/1), the diastereomeric ester mixture gave 1.6 g of (−)-[(E)-1-(2,4-dichlorophenyl)-2-(1,2,4-triazol-1-yl)-4,4-dimethyl-1-penten-3-yl]-(−)-menthoxyacetate ($n_D^{28}$1.5172) as first eluate, 2 g of the diastereomeric ester mixture as second eluate, and 0.7 g of (+)-[(E)-1-(2,4-dichlorophenyl)-2-(1,2,4-triazol-1-yl)-4,4-dimethyl-1-penten-3-yl]-(−)-menthoxyacetate ($n_D^{28}$1.5102) as final eluate.

A mixture of 1.6 g of (−)-[(E)-1-(2,4-dichlorphenyl)-2-(1,2,4-triazol-1-yl)-4,4-dimethyl-1-penten-3-yl]-(−)-menthoxyacetate and 30 cc of a 95% aqueous ethanol solution containing 0.2 g of potassium hydroxide was stirred at 25° C. for one hour. The reaction mixture was poured into 200 cc of ice water and extracted with 300 cc of ethyl acetate. The organic layer was dried over anhydrous sodium sulfate and concentrated in vacuo. The resulting crude crystals were recrystallized from a carbon tetrachloride-n-hexane mixture to obtain 0.8 g of (−)-(E)-1-(2,4-dichlorophenyl)-2-(1,2,4-triazol-1-yl)-4,4-dimethyl-1-penten-3-ol: $[\alpha]_D^{24}$−31.7 (c=1, CHCl$_3$), melting point 160°-161° C. The NMR spectrum was the same as that of the racemate described in Reference Example 2.

Similarly, 0.7 g of (+)-[(E)-1-(2,4-dichlorophenyl)-2-(1,2,4-triazol-1-yl)-4,4-dimethyl-1-penten-3-yl]-(−)-menthoxyacetate was treated with 20 cc of a 90% aqueous ethanol solution containing 0.1 g of potassium hydroxide and the resulting crude crystals were recrystallized from a carbon tetrachloride-n-hexane mixture to obtain 0.3 g of (+)-(E)-1-(2,4-dichlorophenyl)-2-(1,2,4-triazol-1-yl)-4,4-dimethyl-1-penten-3-ol: $[\alpha]_D^{24}$+26.0 (c=1.0, CHCl$_3$); melting point 160°-161° C.

EXAMPLE 3

Asymmetric reduction by use of (+)-menthol.

To a mixture of 0.4 g (0.01 mole) of LiAlH$_4$ and 30 cc of THF, was added at 10° C. 30 cc of a THF solution containing 4.4 g (0.028 mole) of (+)-menthol. To the mixture which has been stirred at room temperature for 30 minutes, was added at −30° C. 50 cc of a THF solution containing 2.0 g (0.007 mole) of 1-(4-chlorophenyl)-2-(1,2,4-triazol-1-yl)-4,4-dimethyl-1-penten-3-one. The resulting mixture was stirred for 2 hours while keeping the temperature at −5° C. After addition of 5 cc of 1 N hydrochloric acid, the insolubles were removed by filtration and the filtrate was poured into 300 cc of ice water and extracted with 500 cc of ethyl ether. The organic layer was washed successively with 200 cc of a saturated aqueous sodium hydrogencarbonate solution and 200 cc of ice-cooled water. The washed organic layer was dried over anhydrous sodium sulfate and concentrated in vacuo to obtain a crude product in oily form. The crude product was purified by silica gel chromatography (100 g of silica gel; developing solvent: n-hexane/acetone=30:1), whereby 0.5 g of unreacted ketone raw material was recovered and 1.0 g of crystals (after crystallizing from a carbon tetrachloride-n-hexane mixture) of (−)-(E)-1-(4-chlorophenyl)-2-(1,2,4-triazol-1-yl)-4,4-dimethyl-1-penten-3-ol were obtained. $[\alpha]_D^{26} - 6.0$ (c=1, CHCl$_3$)

EXAMPLE 4

Asymmetric reduction by use of (+)-2-N,N-dimethylamino-1-phenylethanol.

To a mixture of 0.4 g of LiAlH$_4$ and 20 cc of ethyl ether, while being cooled in ice, was added dropwise 50 cc of an ethyl ether solution containing 1.75 g of (S)-2-dimethylamino-1-phenylethanol. After completion of the addition, the mixture was stirred for 15 minutes, while being kept from cooling. To the mixture was added dropwise 20 cc of an ethyl ether solution containing 2.54 g of N-ethylaniline. After the addition, the mixture was stirred for 3 hours at room temperature. To the mixture was added dropwise at −70° C. 50 cc of an ethyl ether solution containing 1.13 g of (E)-1-(2,4-dichlorophenyl)-2-(1,2,4-triazol-1-yl)-4,4-dimethyl-1-penten-3-one. The mixture was stirred for 3 hours at −73° C. and then left standing overnight at room temperature. To the mixture was added 110 cc of 2 N hydrochloric acid to effect decomposition. The organic layer was separated, washed successively with 100 cc of a saturated aqueous sodium hydrogencarbonate solution and 100 cc of iced water, then dried over anhydrous sodium sulfate, and concentrated in vacuo to obtain 1.26 g of a crystalline triazolyl alcohol compound: $[\alpha]_D^{24} - 16.6$ (c=1.0, CHCl$_3$). The crystalline compound was recrystallized from a cryclohexane-methanol mixture to obtain 0.4 g of (−)-(E)-1-(2,4-dichlorophenyl)-2-(1,2,4-triazol-1-yl)-4,4-dimethyl-1-penten-3-ol: $[\alpha]_D^{24} - 28.8$ (c=1.0, CHCl$_3$), melting point 160°-161° C.

EXAMPLE 5

Asymmetric reduction by use of (+)-2-N-benzyl-N-methylamino-1-phenylethanol:

To a solution of 1.08 g (0.0284 mole) of LiAlH$_4$ in 85 cc of ethyl ether, while being cooled in ice, was added dropwise 22 cc of an ether solution containing 6.86 g (0.0284 mole) of (+)-2-N-benzyl-N-methylamino-1-phenylethanol followed by 40 cc of an ether solution containing 6.90 g (0.0564 mole) of N-ethylaniline. After having been stirred at room temperature for 3 hours, the mixture was cooled to −78° C. To the mixture was added dropwise 55 cc of an ether solution containing 2.75 g (0.0095 mole) of (E)-1-(4-chlorphenyl)-2-(1,2,4-triazol-1-yl)-4,4-dimethyl-1-penten-3-one. The mixture was stirred at said temperature for 3 hours and left standing overnight at room temperature. To the mixture was then added 105 cc of 2 N hydrochloric acid to effect decomposition. The organic layer was separated, washed successively with 100 cc of a saturated aqueous sodium hydrogencarbonate solution and 100 cc of ice-cooled water, then dried over anhydrous sodium sulfate, and concentrated under reduced pressure to obtain 2.83 g of a crude product: $[\alpha]_D^{24} - 6.44$ (c=1.05, CHCl$_3$). A 2.8 g portion of the crude product was recrystallized three times from a cyclohexane-methanol mixture to obtain 0.82 g of (−)-(E)-1-(4-chlorophenyl)-2-(1,2,4-triazol-1-yl)-4,4-dimethyl-1-penten-3-ol: $[\alpha]_D^{24} - 14.9$ (c=1.0, CHCl$_3$).

EXAMPLE 6

Asymmetric reduction by use of (+)-N-methylephedrine:

To a solution of 1.25 g (0.033 mole) of LiAlH$_4$ in 40 cc of ethyl ether, while being cooled in ice, was added 100 cc of an ethyl ether solution containing 6.1 g (0.034 mole) of (+)-N-methylephedrine dropwise over a period of 30 minutes. After the addition, the mixture was stirred for 15 minutes while keeping the temperature constant. To the mixture was then added dropwise 45 cc of an ethyl ether solution containing 8.24 g (0.068 mole) of N-ethylaniline over a period of 30 minutes. After the addition, the mixture was stirred for 2 hours at room temperature for 2 hours. To the mixture was further added 60 cc of an ethyl ether solution containing 2.9 g (0.01 mole) of (E)-1-(4-chlorophenyl)-2-(1,2,4-triazoly-1-yl)-4,4-dimethyl-1-penten-3-one over a period of 15 minutes at −70° C. to −60° C. The mixture was left standing for 4 hours, while keeping the temperature at −73° C., and then admixed with 110 cc of 2 N hydrochloric acid to effect decomposition. The organic layer was separated, washed successively with 100 cc of a saturated aqueous sodium hydrogencarbonate solution and 100 cc of iced water, then dried over anhydrous sodium sulfate, and concentrated under reduced pressure to obtain 2.9 g of crystals of a triazolyl compound: $[\alpha]_D^{24} - 10.1$ (c=1.0, CHCl$_3$). A 2.5 g portion of the crystals was recrystallized twice from a cyclohexane-dioxane mixture to obtain 0.7 g of (−)-(E)-1-(4-chlorophenyl)-2-(1,2,4-triazol-1-yl)-4,4-dimethyl-1-penten-3-ol: $[\alpha]_D^{24} - 15.8$ (c=1.0, CHCl$_3$), melting point 170°-171° C.

EXAMPLE 7

Synthesis of (−)-(E)-1-(2,4-dichlorophenyl)-2-(1,2,4-triazol-1-yl)-4,4-dimethyl-1-penten-3-ol:

Preparative method (1) (Reaction temperature: −15° C.).

Into 10 cc of an ethyl ether solution containing 0.18 g (4.7 mmole) of LiAlH$_4$, was added dropwise 10 cc of an ethyl ether solution containing 0.84 g (4.7 mmole) of (+)-N-methylephedrine over a period of 30 minutes at room temperature, and the mixture was stirred for 20 minutes. To the mixture, while being cooled in ice, was added dropwise 10 cc of an ethyl ether solution containing 1 g (9.4 mmole) of N-methylaniline over a period of 30 minutes, and the mixture was stirred for one hour at room temperature. To the raction mixture cooled at −15° C., was added over a period of 10 minutes 10 cc of an ether solution containing 1 g (3.1 mmole) of (E)-1-(2,4-dichlorophenyl)-2-(1,2,4-triazol-1-yl)-4,4-dimethyl-1-penten-3-one, and the mixture was stirred for 2 hours at −15° C. The mixture was then poured into 100 cc of 1 N hydrochloric acid, extracted with 100 cc of ether, washed successively with an aqueous sodium hydrogencarbonate solution and ice water, dried over anhydrous magnesium sulfate, and stripped of the solvent under reduced pressure. The crystalline residue was collected by filtration using 10 cc of n-hexane and washed to obtain 0.98 g (98% yield) of the captioned compound: $[\alpha]_D^{25} - 28.0$ (c=1, chloroform).

Preparative method (2) (Reaction temperature: 25° C.).

Into 10 cc of an ethyl ether solution containing 0.18 g (4.7 mmole) of LiAlH$_4$, was added dropwise 10 cc of an ethyl ether solution containing 0.84 g (4.7 mmole) of (+)-N-methylephedrine over a period of 30 minutes at room temperature, and the mixture was stirred for additional 20 minutes. To the mixture, was added dropwise 10 cc of an ethyl ether solution containing 1 g (9.4 mmole) of N-methylaniline over a period of 20 minutes, and the mixture was stirred for additional 20 minutes. To the mixture was added dropwise 10 cc of an ethyl ether solution containing 1 g of (E)-1-(2,4-dichlorophenyl)-4,4-dimethyl-2-(1,2,4-triazol-1-yl)-1-penten-3-one over a period of 5 minutes at room temperature (25° C.), and the mixture was stirred for one hour. The reaction solution was poured into 100 cc of 1 N hydrochloric acid and treated in the same manner as described above in preparative method (1) to obtain 0.98 g (98% yield) of the captioned compound: $[\alpha]_D^{25} -27.0$ (c=1, chloroform).

REFERENCE EXAMPLE 1

Synthesis of racemate of (E)-1-(4-chlorophenyl)-2-(1,2,4-triazol-1-yl)-4,4-dimethyl-1-penten-3-ol:

In 50 ml of methanol, was dissolved 2.9 g (0.01 mole) of (E)-1-(4-chlorophenyl)-2-(1,2,4-triazol-1-yl)-4,4-dimethyl-1-penten-3-one (melting point 108°–109° C.) characterized by the NMR spectrum given below. To the solution was added 0.38 g (0.01 mole) of sodium borohydride, while keeping the temperature of the reaction system at 20° C. or below by cooling in ice. To the solution, after having been kept at 20° C. for 3 hours, was added 1 ml of acetic acid to effect decomposition. The organic layer was extracted with 100 ml of ethyl acetate and the extract was washed with 50 ml of a 5% aqueous hydrogencarbonate solution, and dried over anhydrous sodium sulfate. After the removal of the solvent by distillation under reduced pressure, the residue was recrystallized from n-hexane to obtain 2.0 g (69% yield) of the captioned compound having a melting point of 153°–155° C. The elementary analysis and NMR spectrum (determined on a solution in deutero-chloroform and expressed in terms of $\delta$ value) of each compound were as shown below:

(E)-1-(4-chlorophenyl)-2-(1,2,4-triazol-1-yl)-4,4-dimethyl-1-penten-3-one;

| Elementary analysis: | C % | H % | N % | Cl % |
|---|---|---|---|---|
| calculated for $C_{15}H_{16}N_3OCl$ | 62.17 | 5.58 | 14.50 | 12.23 |
| Found | 62.32 | 5.60 | 14.41 | 12.20 |

NMR spectrum: 8.11 (1H, singlet, triazole proteon), 7.90 (1H, singlet, triazol proton), 7.15 (4H, singlet, phenyl proton), 6.99 (1H, singlet, olefin proton), 0.99 (9H, singlet, butyl proton).

(E)-1-(4-chlorophenyl)-2-(1,2,4-triazol-1-yl)-4,4-dimethyl-1-penten-3-ol:

| Elementary analysis: | C % | H % | N % | Cl % |
|---|---|---|---|---|
| Calculated for $C_{15}H_{18}N_3OCl$ | 61.74 | 6.23 | 14.40 | 12.15 |
| Found | 61.82 | 6.38 | 14.38 | 12.15 |

NMR spectrum: 8.52 (1H, singlet, triazole proton), 7.98 (1H, singlet, triazole proton), 7.30 (4H, singlet, phenyl proton), 6.91 (1H, singlet, olefin proton), 4.56 (2H, broad singlet, hydroxyl proton and proton of methyne group bearing hydroxyl group), 0.66 (9H, singlet, butyl proton)

REFERENCE EXAMPLE 2

Synthesis of (E)-1-(2,4-dichlorophenyl)-2-(1,2,4-triazol-1-yl)-4,4-dimethyl-1-penten-3-ol racemate:

To 50 cc of a methanol solution containing 3.2 g of (E)-1-(2,4-dichlorophenyl)-2-(1,2,4-triazol-1-yl)-4,4-dimethyl-1-penten-3-one (melting point 92°–93° C.) characterized by the NMR spectrum shown below, was added 0.5 g of sodium borohydride, while cooling in ice. The mixture was then stirred at room temperature for 3 hours and treated as in Reference Example 1 to obtain 2.6 g of the captioned compound melting at 148°–149° C.

The NMR spectra were shown below in terms of $\delta$ value measured on a deutero-chloroform solution.

(E)-1-(2,4-dichlorophenyl)-2-(1,2,4-triazol-1-yl)-4,4-dimethyl-1-penten-3-one:

8.30 (1H, singlet, triazole proton), 8.04 (1H, singlet, triazole proton), 7.45 (1H, multiplet, phenyl proton), 7.26 (2H, multiplet, phenyl proton), 7.22 (1H, singlet, olefin proton), 0.97 (9H, singlet, butyl proton).

(E)-1-(2,4-dichlorophenyl)-2-(1,2,4-triazol-1-yl)-4,4-dimethyl-1-penten-3-ol:

8.45 (1H, singlet, triazole proton), 7.97 (1H, singlet, triazole proton), 7.80 (3H, multiplet, phenyl proton), 6.80 (1H, singlet, olefin proton), 4.35 (2H, broad singlet, hydroxyl proton and hydroxyl group-bearing methyne proton), 0.63 (9H, singlet, tert-butyl proton).

EXAMPLE 8

Synthesis of (+)-(E)-1-(4-chlorophenyl)-2-(1,2,4-triazol-1-yl)-4,4-dimethyl-1-penten-3-ol by asymmetric reduction:

Into 40 cc of an ethyl ether solution containing 1.25 g (0.033 mole) of LiAlH$_4$, while being cooled in ice, was added dropwise over a period of 30 minutes 100 cc of an ethyl ether solution containing 6.1 g (0.034 mole) of (−)-N-methylephedrine, and the mixture was then stirred at room temperature for 15 minutes. To the mixture was added dropwise over a period of 30 minutes 45 cc of an ethyl ether solution containing 8.24 g (0.068 mole) of N-ethylaniline, and the resulting mixture was stirred at room temperature for 3 hours. To the mixture was further added 60 cc of an ethyl ether solution containing 2.9 g (0.01 mole) of (E)-1-(4-chlorophenyl)-2-(1,2,4-triazol-1-yl)-4,4-dimethyl-1-penten-3-one over a period of 12 minutes at −70° to −67° C., and the mixture was stirred at −73° C. for 3 hours under adiabatic conditions. The mixture was left standing overnight at room temperature, and to the mixture was added 110 cc of 2 N hydrochloric acid to effect decomposition. The separated organic layer was washed with 100 cc of a saturated aqueous sodium hydrogencarbonate solution, then with 100 cc of ice water, dried over anhydrous sodium sulfate and concentrated under reduced pressure to obtain 3.0 g of crystals of a triazolyl alcohol compound: $[\alpha]_D^{24} +9.0$ (c=1.0, CHCl$_3$). A 2.5 g portion of the obtained crystals was recrystallized twice from a cyclohexane-dioxane mixture to obtain 0.81 g of (+)-(E)-1-(4-chlorophenyl)-2-(1,2,4-triazol-1-yl)-4,4-dimethyl-1-penten-3-ol:

$[\alpha]_D^{24} +15.7$ (c=1.0, CHCl$_3$); melting point 169°–170° C. The NMR spectrum was identical with that of the racemate shown in Reference Example 1.

EXAMPLE 9

Synthesis of (+)-(E)-1-(2,4-dichlorophenyl)-2-(1,2,4-triazol-1-yl)-4,4-dimethyl-1-penten-3-ol by asymmetric reduction:

A chiral metal-hydrogen complex was formed in a manner similar to that in Example 1 by adding to 20 cc of an ethyl ether solution containing 0.63 g of LiAlH$_4$ 50 cc of an ethyl ether solution containing 3.05 g of N-methylephedrine followed by 20 cc of an ethyl ether solution containing 4.12 g of N-ethylaniline. To the resulting solution, was added at $-70°$ C. 30 cc of an ethyl ether solution containing 1.62 g of (E)-1-(2,4-dichlorophenyl)-2-(1,2,4-triazol-1-yl)-4,4-dimethyl-1-penten-3-one. The resulting mixture was stirred at $-73°$ C. for 5 hours under adiabatic conditions and left standing overnight at room temperature. To the mixture was added 60 cc of 2 N hydrochloric acid to effect decomposition. The organic layer was washed successively with 100 cc of a saturated sodium hydrogencarbonate solution and 100 cc of ice-cooled water, dried over anhydrous sodium sulfate, and concentrated under reduced pressure to obtain 1.82 g of crude crystals. The crude crystals were recrystallized three times from a cyclohexane-methanol mixture to obtain 0.41 g of (+)-(E)-1-(2,4-dichlorophenyl)-2-(1,2,4-triazol-1-yl)-4,4-dimethyl-1-penten-3-ol: $[\alpha]_D^{24}+29.2$ (c=1.0, CHCl$_3$); melting point $160°-161°$ C. The NMR spectrum was identical with that of the racemate described in Reference Example 2.

EXAMPLE 10

Asymmetric reduction by use of (−)-menthol:

To 0.4 g (0.01 mole) of LiAlH$_4$ dissolved in 30 cc of THF, was added at $10°$ C. 30 cc of a THF solution containing 4.4 g (0.028 mole) of (−)-menthol. The mixture was then stirred at room temperature for 30 minutes. To the mixture was added at $-30°$ C. 50 cc of a THF solution containing 2.0 g (0.007 mole) of 1-(4-chlorophenyl)-2-(1,2,4-triazol-1-yl)-4,4-dimethyl-1-penten-3-one. The mixture was then stirred for 2 hours while keeping the temperature at $-5°$ C. After adding to the mixture 5 cc of 1 N hydrochloric acid and removing the insolubles by filtration, the filtrate was poured into 300 cc of ice water and extracted with 500 cc of ethyl ether. The organic layer was washed with 200 cc of a saturated sodium hydrogencarbonate solution, then with 200 cc of ice-cooled water, dried over anhydrous sodium sulfate, and concentrated under reduced pressure to obtain a crude oily product. The crude product was fractionally purified by silica gel column chromatography (100 g silica gel; developing solvent: n-hexane/acetone=30/1). There was obtained 0.5 g of unreacted ketone compound which was recovered and 1.3 g of crystals of (+)-(E)-1-(4-chlorophenyl)-2-(1,2,4-triazol-1-yl)-4,4-dimethyl-1-penten-3-ol (by crystallization from a carbon tetrachloride-n-hexane mixture): $[\alpha]_D^{26}+5.0$ (c=1, CHCl$_3$).

EXAMPLE 11

Asymmetric reduction by use of (−)-borneol.

To 0.2 g (0.0053 mole) of LiAlH$_4$ dissolved in 30 cc of THF, was added at $0°$ C. 30 cc of a THF solution containing 2.4 g (0.0155 mole) of (+)-borneol. The mixture was then stirred at room temperature for 50 minutes. To the mixture was added at $0°$ C. 30 cc of a THF solution containing 1.0 g (0.0034 mole) of (E)-1-(4-chlorophenyl)-2-(1,2,4-triazol-1-yl)-4,4-dimethyl-1-penten-3-one. The mixture was then stirred at room temperature for 3 hours. After adding 0.5 cc of 1 N hydrochloric acid to the mixture and removing the insolubles by filtration, the filtrate was poured into 300 cc of ice-cooled water, and extracted with 500 cc of ethyl ether. The organic layer was washed with 200 cc of a saturated aqueous sodium hydrogencarbonate solution, then with 200 cc of ice-cooled water, dried over anhydrous sodium sulfate, and concentrated under reduced pressure to obtain a crude oily substance. The crude substance was fractionally purified by silica gel column chromatography (100 g silica gel; developing solvent: n-hexane/acetone=30/1). There were obtained 0.4 g of the unreacted ketone which was recovered and 0.45 g of crystals of (+)-(E)-1-(4-chlorophenyl)-2-(1,2,4-triazol-1-yl)-4,4-dimethyl-1-penten-3-ol (by crystallization from a carbon tetrachloride-n-hexane mixture): $[\alpha]_D^{24}+3.2$ (c=1, CHCl$_3$).

The useful properties of the (−)-triazolyl alcohol derivatives of this invention are illustrated below in detail with reference to some examples of tests performed on (−)-(E)-(4-chlorophenyl)-2-(1,2,4-triazol-1-yl)-4,4-dimethyl-1-penten-3-ol (compound No. 1) obtained in Example 1 and (−)-(E)-1-(2,4-dichlorophenyl)-2-(1,2,4-triazol-1-yl)-4,4-dimethyl-1-penten-3-ol (compound No. 2) obtained in Example 2, using as reference samples corresponding (+)-triazolyl alcohol derivatives obtained in Examples 1 and 2 (compounds No. 3 and No. 4, respectively) and the racemates obtained in Reference Examples 1 and 2 (compounds No. 5 and No. 6, respectively).

TEST EXAMPLE 1

Inhibition of fungus growth:

A medium containing 5 g of polypeptone, 20 g of malt extract, 20 g of sucrose and 20 g of agar per liter of water heated to form a liquid. To the liquefied medium, was added a predetermined quantity of a diluted sample of the test compound in the form of emulsifiable concentrate so as to keep the concentration of each sample in the medium at a predetermined level. After thorough stirring, the medium was poured into a Petri dish to form an agar plate. After the agar had set, it was inoculated with a colony or a conidium suspension of the test fungus. The fungus species and the incubation period (the period of time from inoculation to observation) were as shown below. The incubation temperature was $20°$ C. for *Venturia inaequalis* and $28°$ C. for other fungi.

| Fungus species | Abbreviation | Incubation period (day) |
|---|---|---|
| *Helminthosporium gramineum* | Hg | 6 |
| *Penicillium italicum* | Pi | 6 |
| *Venturia inaequalis* | Vi | 7 |
| *Valsa mali* | Vm | 4 |
| *Mycosphaerella melonis* | Mm | 4 |
| *Diaporthe citri* | Dc | 6 |
| *Ustilago nuda* | Un | 6 |
| *Verticillium albo-atrum* | Va | 7 |
| *Septoria tritici* | St | 7 |
| *Cercospora beticola* | Cb | 7 |

The fungus growth inhibitory activity of the test compound was evaluated by the concentration which inhibits 90% of the mycelium growth (ED$_{90}$). As is seen from the results shown in Table 1, it was found that triazolyl alcohol derivatives of this invention (compounds No. 1 and No. 2) show markedly superior antifungal spectra compared with (+)-triazolyl alcohol derivatives (compounds No. 3 and No. 4) and racemates (compounds No. 5 and No. 6).

TABLE 1

Concentration, in ppm, which inhibits 90% colony growth (ED$_{90}$).

| Fungus species | Compound of this invention | | Reference compound | | | |
|---|---|---|---|---|---|---|
| | No. 1 | No. 2 | No. 3 | No. 4 | No. 5 | No. 6 |
| Hg | 1.5 | 1.5 | >25.0 | >25.0 | 6.0 | 6.0 |
| Pi | 0.1 | 0.2 | >25.0 | >25.0 | 0.4 | 1.0 |
| Vi | <0.1 | <0.1 | 25.0 | 25.0 | 0.1 | 0.1 |
| Vm | 0.1 | <0.1 | >25.0 | >25.0 | 0.4 | 0.1 |
| Mn | 0.3 | 0.2 | >25.0 | >25.0 | 1.3 | 1.0 |
| Dc | 0.4 | 1.0 | >25.0 | >25.0 | 5.0 | 5.0 |
| Un | 5.0 | 5.0 | >25.0 | >25.0 | 5.0 | 5.0 |
| Va | 0.4 | 0.4 | >25.0 | >25.0 | 1.3 | 1.3 |
| St | 0.4 | 0.1 | >25.0 | >25.0 | 1.0 | 0.4 |
| Cb | 0.4 | 0.4 | >25.0 | >25.0 | 1.5 | 1.5 |

TEST EXAMPLE 2

Control effect on leaf spot of peanut:

A 85-ml plastic pot filled with sandy loam was seeded with peanut (var. Semi-upright) at a rate of 1 seed/pot and the seed was cultivated in an air-conditioned greenhouse at 25° to 30° C. for 12 days to obtain the young peanut seedling grown to the stage of the third foliage leaf. At this stage a diluted liquor of an emulsifiable concentrate of each test compound was sprayed over the foliage at a rate of 10 ml/pot. After air-drying, the seedling was inoculated with *Cercospora personata*, then covered with a sheet of polyvinyl chloride film to maintain the humidity, and left standing in an air-conditioned greenhouse at 25° to 30° C. In order to develop at full severity of the disease, the seedling was further cultivated for 10 days in said greenhouse. The foliage of each seedling was then inspected for the symptoms of disease and the severity was calculated in the following way: the appearance of the lesion on the inspected leaf was classified into 5 indices, that is, 0, 0.5, 1, 2 and 4, and the disease severity was calculated by the equation given below.

| Lesion index | Appearance of lesion |
|---|---|
| 0 | Neither colony nor lesion was observed. |
| 0.5 | Colony or lesion of less than 5% in area based on total leaf area was observed on the leaf surface. |
| 1 | Colony or lesion of less than 20% in area based on total leaf area was observed on the leaf surface. |
| 2 | Colony or lesion of less than 50% in area based on total leaf area was observed on leaf surface. |
| 4 | Colony or lesion of 50% or more in area based on total leaf area was observed on leaf surface. |

$$\text{Severity (\%)} = \frac{\Sigma(\text{lesion index}) \times (\text{number of leaves})}{(\text{Number of inspected leaves}) \times 4} \times 100$$

Then, the control value was obtained by the following equation:

$$\text{Control value (\%)} = 100 - \frac{\text{Severity in treated plot}}{\text{Severity in control plot}} \times 100$$

As shown in Table 2, the test results revealed that the (−)-triazolyl alcohol derivative exhibits a far higher control effect as compared with the (+)-triazolyl alcohol derivative and the racemate.

TABLE 2

| Compound No. | Concentration of active ingredient (ppm) | Control value (%) |
|---|---|---|
| The present compounds: | | |
| 1 | 12.5 | 100 |
| | 3.1 | 100 |
| 2 | 12.5 | 100 |
| | 3.1 | 100 |
| Reference compounds: | | |
| 3 | 12.5 | 0 |
| | 3.1 | 0 |
| 4 | 12.5 | 0 |
| | 3.1 | 0 |
| 5 | 12.5 | 91 |
| | 3.1 | 40 |
| 6 | 12.5 | 97 |
| | 3.1 | 50 |

TEST EXAMPLE 3

Control effect (curative effect) on brown rust of wheat in the test on young seedling:

A 85-ml plastic pot filled with sandy loam was seeded with the seed of wheat (var. Norin No. 61) at a rate of 10 to 15 seeds per pot and cultivated for 7 days in an air-conditioned greenhouse at 18° to 23° C. to allow the young wheat seedlings to grow to the developmental stage of first foliage. The seedlings at this stage was inoculated with *Puccinia recondita* and left standing in a humidified chamber at 23° C. for 16 hours to become infected with the fungus. A diluted emulsion of the test compound was then sprayed at a rate of 10 ml per pot. The pot with seedlings was kept in a constant temperature chamber at 23° C., cultivated for 10 days under radiation from a fluorescent lamp, and the symptoms on the first leaf was observed. The method of examining the symptoms and the method of calculating the control vaue were the same as in Test Example 2.

As shown in Table 3, the test results revealed that a (−)-triazolyl alcohol derivative exhibits a much higher control effect as compared with not only a (+)-triazolyl alcohol derivative but also a racemate.

TABLE 3

| Compound No. | Concentration of active ingredient (ppm) | Control value (%) |
|---|---|---|
| The present compounds: | | |
| 1 | 0.8 | 100 |
| | 0.2 | 100 |
| 2 | 0.8 | 100 |
| | 0.2 | 100 |
| Reference compounds: | | |
| 3 | 0.8 | 0 |
| | 0.2 | 0 |
| 4 | 0.8 | 0 |
| | 0.2 | 0 |
| 5 | 0.8 | 84 |
| | 0.2 | 57 |

TABLE 3-continued

| Compound No. | Concentration of active ingredient (ppm) | Control value (%) |
| --- | --- | --- |
| 6 | 0.8 | 90 |
|   | 0.2 | 70 |

TEST EXAMPLE 4

Control effect (curative effect) on scab of apple in the test on seedling:

A 85-ml plastic pot filled with sandy loam was seeded with 2 or 3 apple seeds and cultivated in an air-conditioned chamber at 23° to 28° C. for 30 days to obtain seedlings in the fifth or sixth foliage stage. The seedling at this stage was inoculated with *Venturia inaequalis* and left standing in a humidified dark chamber (90% or higher relative humidity) at 15° C. to become infected with the fungus. Four days after that, an aqueous dilute liquor of the test compound in emulsifiable concentrate form was sprayed over the foliage at a rate of 10 ml per pot. The pot was left standing for 20 to 21 days in a constant temperature chamber at 15° C. under illumination and humidification. The foliage was then inspected for the symptoms of disease. The examination of disease severity and the calculation of control value were performed as in Test Example 2.

As shown in Table 4, the test results revealed that the control effect of a (−)-triazolyl alcohl derivative was far superior to that of a (+)-triazolyl alcohol deirvative and even higher than that of a racemate.

TABLE 4

| Compound No. | Concentration of active ingredient (ppm) | Control value (%) |
| --- | --- | --- |
| The present compounds: | | |
| 1 | 3.1 | 100 |
|   | 0.8 | 50 |
| 2 | 3.1 | 100 |
|   | 0.8 | 100 |
| Reference compounds: | | |
| 3 | 3.1 | 0 |
|   | 0.8 | 0 |
| 4 | 3.1 | 0 |
|   | 0.8 | 0 |
| 5 | 3.1 | 87 |
|   | 0.8 | 0 |
| 6 | 3.1 | 95 |
|   | 0.8 | 20 |

For reference, the results of examination on the plant growth regulatory activity and the herbicidal activity are given below. It was shown that the said activities of (+)-triazolyl alcohol derivatives and racemates are far higher than those of (−)-triazolyl alcohol derivatives.

TEST EXAMPLE 5

Test on wheat for growth retardation:

A 85-ml plastic pot filled with sandy loam was seeded with 10 to 15 seeds of wheat (var. Chikugo No. 2), which had been soaked in an aqueous diluted liquor of the test compound in emulsifiable concentrate form, and cultivated at a controlled temperature of 18° to 23° C. for 7 days. The leaf length was then measured and the percentage elongation was obtained by comparison with the leaf length in the control plot.

$$\text{Elongation (\%)} = \frac{\text{Plant length in treated plot}}{\text{Plant length in control plot}} \times 100$$

The test results were as shown in Table 5. It was found that the plant growth retarding activity of the (−)-triazolyl alcohol derivative is far lower than that of the (+)-triazolyl alcohol derivative or a racemate.

TABLE 5

| Compound No. | Concentration of treating liquor (ppm) | Plant length (mm) | Elongation (%) |
| --- | --- | --- | --- |
| The present compounds: | | | |
| 1 | 12.5 | 95 | 69 |
|   | 3.1 | 115 | 83 |
| 2 | 12.5 | 133 | 96 |
|   | 3.1 | 138 | 100 |
| Reference compounds: | | | |
| 3 | 12.5 | 45 | 33 |
|   | 3.1 | 61 | 44 |
| 4 | 12.5 | 75 | 54 |
|   | 3.1 | 95 | 69 |
| 5 | 12.5 | 62 | 45 |
|   | 3.1 | 83 | 60 |
| 6 | 12.5 | 90 | 65 |
|   | 3.1 | 105 | 76 |
| Control (untreated) | — | 138 | 100 |

The useful properties of the (+)-triazolyl alcohol derivative are described below in detail with reference to some examples of tests performed on (+)-(E)-1-(4-chlorophenyl)-2-(1,2,4-triazol-1-yl)-4,4-dimethyl-1-penten-3-ol (compound No. 3) obtained in Example 1 and (+)-(E)-1-(2,4-dichlorophenyl)-(1,2,4-triazol-1-yl)-4,4-dimethyl-1-penten-3-ol (compound No. 4) obtained in Example 2, using as reference samples corresponding (−)-triazolyl alcohol derivatives obtained in Examples 1 and 2 (compound No. 1 and No. 2, respectively) and the racemates obtained in Reference Examples 1 and 2 (compound No. 5 and No. 6, respectively).

TEST EXAMPLE 6

Dwarfing test on pot-mum:

Pot-mum (var. Paragon) was cultivated in a 4.8-inch clay pot filled with 500 g of an artificial soil composed of sea sand, mountain soil and peat. Two weeks after setting, the plant was pinched so as to undergo the triple stem training. Two weeks after pinching, when sprouting had already begun, the test compound diluted to a predetermined concentration was applied to the plant and the growth retarding effect was inspected 42 days after the treatment. The results were as shown in Table 6. The effect was evaluated in the following way: the difference between the plant height at the time of application of the chemical and the plant height on the 42nd day after the application is recorded and expressed as elongation index which is the percentage of said difference based on the similar difference in the untreated plot. The indices shown in Table 6 were mean values of three replications.

All of the test compounds showed inhibition of internode elongation and reduction in plant height, but the phytotoxicity such as necrosis or chlorisis was not observed and even the green color of leaves became deeper. The (+)-triazolyl alcohol derivatives (compound No. 3 and No. 4) showed a far stronger dwarfing effect compared with the (−)-triazolyl alcohol derivatives (compound No. 1 and No. 2) and a stronger effect compared with the racemates (compound No. 5 and No. 6).

TABLE 6

Dwarfing test on pot-mum.

| Compound No. | Concentration of treating solution (ppm) | Elongation index (%) |
|---|---|---|
| The present Compound: | | |
| 3 | 200 | 15 |
|  | 100 | 23 |
|  | 50 | 39 |
| 4 | 200 | 48 |
|  | 100 | 79 |
|  | 50 | 91 |
| Reference compounds: | | |
| 1 | 200 | 88 |
|  | 100 | 94 |
|  | 50 | 103 |
| 2 | 200 | 90 |
|  | 100 | 101 |
|  | 50 | 103 |
| 5 | 200 | 21 |
|  | 100 | 42 |
|  | 50 | 78 |
| 6 | 200 | 63 |
|  | 100 | 95 |
|  | 50 | 101 |

TEST EXAMPLE 7

Test on apple seedling for growth retardation of current shoot:

An apple seedling (var. Golden Delicious) planted in a 18-cm clay pot was pruned and cultivated in a greenhouse. Three weeks after the emergence of current shoots, the above-ground part of the plant was entirely treated with a liquid preparation of the test compound in predetermined concentration by means of a handsprayer. Fourteen days after the treatment, the lengths of current shoots were measured and the amount of elongation was obtained from the difference between said length and the length at the time of chemical treatment. Two pots of the plant were used for each chemical treatment and the growth length determined on 4 to 6 shoots. The results in average value were as shown in Table 7. The (+)-triazolyl alcohol derivatives showed a far higher growth inhibitory activity as compared with the (−)-triazolyl alcohol derivatives and racemates.

TABLE 7

Test on apple tree for growth retardation of current shoot.

| Compound No. | Concentration of treating liquor (ppm) | Elongation (mm) | (%) |
|---|---|---|---|
| The present compounds: | | | |
| 3 | 100 | 33 | 18 |
|  | 50 | 64 | 36 |
|  | 25 | 79 | 44 |
| 4 | 100 | 120 | 67 |
|  | 50 | 147 | 82 |
|  | 25 | 163 | 91 |
| Reference compounds: | | | |
| 1 | 100 | 189 | 106 |
|  | 50 | 168 | 94 |
|  | 25 | 185 | 103 |
| 2 | 100 | 171 | 96 |
|  | 50 | 176 | 98 |

TABLE 7-continued

Test on apple tree for growth retardation of current shoot.

| Compound No. | Concentration of treating liquor (ppm) | Elongation (mm) | (%) |
|---|---|---|---|
|  | 25 | 180 | 101 |
| 5 | 100 | 65 | 36 |
|  | 50 | 78 | 44 |
|  | 25 | 93 | 52 |
| 6 | 100 | 160 | 89 |
|  | 50 | 172 | 96 |
|  | 25 | 172 | 96 |
| Control (untreated) | — | 179 | 100 |

TEST EXAMPLE 8

Test on lawn grass for growth retardation:

A 1/5,000—are Wagner pot filled with upland soil was seeded with seeds of lawn grass (var. Seaside grass). After covering with soil, the seeds were cultivated in a greenhouse. After one month, the grass was cut at a height of 1 cm from the ground level and both foliage and soil were treated with a predetermiend amount of the chemical preparation by using a hand sprayer. Two weeks after the treatment, the elongation of grass was examined, then the grass was cut again and the cultivation was continued for additional 4 weeks. The results of examination performed after two weeks (first examination) and four weeks (second examination) from the treatment were as shown in Table 8. As compared with the (−)-triazolyl alcohol derivatives and racemates, the (+)-triazolyl alcohol derivatives showed a far greater effect.

TABLE 8

Test on lawn grass for growth retardation.

| Compound No. | Application rate (g/are) | Growth of lawn grass (cm) | | |
|---|---|---|---|---|
| | | 1st time | 2nd time | Total |
| The present compounds: | | | | |
| 3 | 10 | 1.0 | 0.5 | 1.5 |
|  | 5 | 1.3 | 0.5 | 1.8 |
|  | 2.5 | 1.5 | 1.0 | 2.5 |
| 4 | 10 | 2.0 | 3.0 | 5.0 |
|  | 5 | 3.0 | 3.5 | 6.5 |
|  | 2.5 | 3.8 | 4.8 | 8.6 |
| Reference compounds: | | | | |
| 1 | 10 | 4.3 | 8.0 | 12.3 |
|  | 5 | 4.5 | 8.5 | 13.0 |
|  | 2.5 | 5.0 | 9.0 | 14.0 |
| 2 | 10 | 4.5 | 8.5 | 13.0 |
|  | 5 | 4.5 | 9.0 | 13.5 |
|  | 2.5 | 5.0 | 9.0 | 14.0 |
| 5 | 10 | 1.5 | 1.0 | 2.5 |
|  | 5 | 1.8 | 2.0 | 3.8 |
|  | 2.5 | 2.0 | 3.0 | 5.0 |
| 6 | 10 | 2.5 | 3.3 | 5.8 |
|  | 5 | 3.8 | 3.3 | 7.1 |
|  | 2.5 | 4.0 | 6.0 | 10.0 |
| Untreated | — | 5.0 | 9.0 | 14.0 |

TEST EXAMPLE 9

Pot test of naked barley:

A 1/2,000—are Wagner pot was filled with paddy soil of the plough layer, which passed through a wire screen having a square aperture of 1.5×1.5 cm. After applying as basal fertilizer a urea-base compound fertilizer at an application rate of N/P$_2$O$_5$/K$_2$O=1.3/1.3/1.3 g/pot, the pot was seeded with 12 seeds of naked barley (var. Hinodehadaka) on December 5. The seeds were cultivated in a greenhouse. When the seedling had emerged and grown to a height of several centimeters, the seedlings were thinned to 6 stumps per pot. At the beginning of internode elongation (Feb. 15), a predetermiend amount of the chemical preparation was sprayed over the soil surface and the cultivation was further continued until the harvest time (May 21) had reached when the plant height, number of ear, and the weight of husked barley were measured. The results of examination were as shown in Table 9. Although all of the test compounds showed a dwarfing, tiller-promoting, and yield increasing effect, the (+)-triazolyl alcohol derivative exhibited much superior effect compared with the (−)-triazolyl alcohol derivative and a stronger dwarfing effect compared with the racemate.

TABLE 9

Pot test of naked barley.

| Compound No. | Application rate, active ingredient (g/are) | Number of ear (per pot) | Plant height (cm) | Weight of husked barley (g/pot) | (%) |
|---|---|---|---|---|---|
| The present compounds: | | | | | |
| 3 | 1 | 58.0 | 64.7 | 71.7 | 118 |
|  | 5 | 60.0 | 50.4 | 66.2 | 109 |
| 4 | 1 | 48.3 | 79.7 | 64.6 | 107 |
|  | 5 | 53.3 | 72.3 | 62.4 | 103 |
| Reference compounds: | | | | | |
| 1 | 1 | 46.7 | 88.7 | 60.0 | 99 |
|  | 5 | 48.7 | 75.3 | 61.2 | 101 |
| 2 | 1 | 45.0 | 86.1 | 59.6 | 98 |
|  | 5 | 46.7 | 82.4 | 59.8 | 99 |
| 3 | 1 | 57.7 | 76.4 | 74.3 | 123 |
|  | 5 | 60.0 | 54.3 | 67.3 | 111 |
| 4 | 1 | 47.4 | 83.5 | 63.1 | 104 |
|  | 5 | 49.0 | 80.1 | 62.4 | 103 |
| Untreated | — | 45.3 | 85.9 | 60.6 | 100 |

TEST EXAMPLE 10

Weed control test in upland soil:

A 1/1,000—are Wagner pot was filled with a soil mixed with seeds of large crabgrass, green amaranth, and fat hen. A diluted aqueous emulsion containing a prescribed quantity of the test compound was applied by means of a hand sprayer to treat the soil surface. After the treatment, sugar beet seedlings (var. Monohill) in fifth leaf age bred in a paper pot were transplanted to the Wagner pot and bred in a greenhouse. The weed control activity and phytotoxicity of the test compound were observed on 20th day from the treatment. The results of observation were as shown in Table 10.

The evaluation of weed control activity was performed by classifying the observed results into the following 6 grades of from 0 to 5.

The phytotoxicity was evaluated likewise.

| | Degree of weed control (%) |
|---|---|
| 0 | 0–9 |
| 1 | 10–29 |
| 2 | 30–49 |
| 3 | 50–69 |
| 4 | 70–89 |
| 5 | 90–100 |

TABLE 10

Weed control test in upland soil.

| Compound No. | Application rate (g/are) | Large crabgrass | Green amaranth | Fat hen | Phytotoxicity to sugar beet |
|---|---|---|---|---|---|
| The present compounds: | | | | | |
| 3 | 20 | 5 | 5 | 5 | 0 |
|  | 10 | 5 | 5 | 5 | 0 |
| 4 | 20 | 5 | 5 | 5 | 0 |
|  | 10 | 4 | 5 | 5 | 0 |
| Reference compounds: | | | | | |
| 1 | 20 | 4 | 4 | 5 | 0 |
|  | 10 | 3 | 3 | 4 | 0 |
| 2 | 20 | 3 | 3 | 3 | 0 |
|  | 10 | 3 | 3 | 3 | 0 |
| 5 | 20 | 5 | 5 | 5 | 0 |
|  | 10 | 4 | 5 | 5 | 0 |
| 6 | 20 | 4 | 5 | 5 | 0 |
|  | 10 | 4 | 4 | 5 | 0 |

The results of test for the fungicidal activity of the present compounds are described below for reference. The fungicidal activity of the (+)-triazolyl alcohol derivative was far higher than those of the (−)-triazolyl alcohol derivative and the racemate.

PREPARATION EXAMPLE 1 DUST

Two parts of the compound No. 1, 88 parts of clay and 10 parts of talc are thoroughly mixed by grinding to form a dust preparation containing 2% of the active ingredient.

PREPARATION EXAMPLE 2 DUST

Three parts of the compound No. 2, 67 parts of clay and 30 parts of talc are thoroughly mixed by grinding to form a dust preparation containing 3% of the active ingredient.

PREPARATION EXAMPLE 3 WETTABLE POWDER

Thirty parts of the compound No. 1, 45 parts of diatomaceous earth, 20 parts of white carbon, 3 parts of a wetting agent (sodium lauryl sulfate) and 2 parts of a dispersant (calcium ligninsulfonate) are throughly mixed by grinding to form a wettable powder preparation containing 30% of the active ingredient.

PREPARATION EXAMPLE 4 WETTABLE POWDER

Fifty parts of the compound No. 2, 45 parts of diatomaceous earth, 2.5 parts of a wetting agent (calcium alkylbenzenesulfonate) and 2.5 parts of a dispersant (calcium ligninsulfonate) are thoroughly mixed by grinding to form a wettable powder preparation containing 50% of the active ingredient.

PREPARATION EXAMPLE 5 EMULSIFIABLE CONCENTRATE

Ten parts of the compound No 1, 80 parts of cyclohexanone and 10 parts of an emulsifier (polyoxyethylene alkylaryl ether) are mixed to form an emulsifiable concentrate containing 10% of the active ingredient.

PREPARATION EXAMPLE 6 GRANULE

Five parts by weight of the compound No. 2, 40 parts by weight of bentonite, 50 parts by weight of clay and 5 parts by weight of sodium ligninsulfonate are thoroughly mixed by grinding. The resulting mixture is sufficiently milled together with water, then granulated and dried to yield a granule preparation.

PREPARATION EXAMPLE 7 DUST

Two parts of the compound No. 3, 88 parts of clay and 10 parts of talc are thoroughly mixed by grinding to form a dust preparation containing 2% of the active ingredient.

PREPARATION EXAMPLE 8 DUST

Three parts of the compound No. 4, 67 parts of clay and 30 parts of talc are thoroughly mixed by grinding to form a dust preparation containing 3% of the active ingredient.

PREPARATION EXAMPLE 9 WETTABLE POWDER

Thirty parts of the compound No. 3, 45 parts of diatomaceous earth, 20 parts of white carbon, 3 parts of a wetting agent (sodium lauryl sulfate) and 2 parts of a dispersant (calcium ligninsulfonate) are thoroughly mixed by grinding to form a wettable powder preparation containing 30% of the active ingredient.

PREPARATION EXAMPLE 10 WETTABLE POWDER

Fifty parts of the compound No. 4, 45 parts of diatomaceous earth, 2.5 parts of a wetting agent (calcium alkylbenzenesulfonate) and 2.5 parts of a dispersant (calcium ligninsulfonate) are thoroughly mixed by grinding to form a wettable powder containing 50% of the active ingredient.

PREPARATION EXAMPLE 11 EMULSIFIABLE CONCENTRATE

Ten parts of the compound No 3, 80 parts of cyclohexanone and 10 parts of an emulsfier (polyoxyethylene alkylaryl ether) are mixed to form an emulsifiable concentrate containing 10% of the active ingredient.

PREPARATION EXAMPLE 12 GRANULE

Five parts by weight of the compound No. 4, 40 parts by weight of bentonite, 50 parts by weight of clay and 5 parts by weight of sodium ligninsulfonate are thoroughly mixed by grinding, then thoroughly milled together with water, granulated, and dried to form a granule preparation.

PREPARATION EXAMPLE 13 LIQUID 0.05 Parts by weight of the compound No. 3, 1 part by weight of "Hymal 1009" (a surfactant produced by Matsumoto Yushi Co.), 1 part by weight of "Newcol 560" (a nonionic emulsifier), 2.5 parts by weight of cyclohexanone and 95.45 parts by weight of water are mixed to form a liquid preparation.

What is claimed is:

1. A substantially pure triazolyl alcohol derivative represented by the general formula:

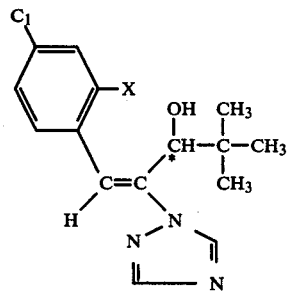

wherein X represents a hydrogen atom or a chlorine atom and the asterisk indicates an asymmetric carbon atom, and having an optical activity of (−) or (+).

2. A triazolyl alcohol derivative according to claim 1, wherein the optical activity is (−).

3. A triazolyl alcohol derivative according to claim 1, wherein the optical activity is (+).

4. A triazolyl alcohol derivative according to claim 2, wherein X represents a chlorine atom.

5. A triazolyl alcohol derivative according to claim 3, wherein X represents a hydrogen atom.

6. A fungicidal composition comprising an inert carrier and as an active ingredient, a fungicidally effective amount of a substantially pure triazolyl alcohol derivative represented by the general formula:

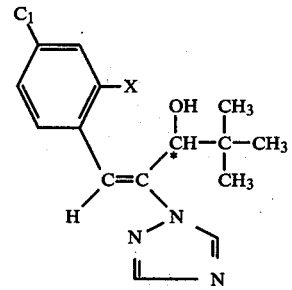

wherein X represents a hydrogen atom or a chlorine atom and the asterisk indicates an asymmetric carbon atom and having an optical activity of (−).

7. A plant growth regulatory or herbicidal composition comprising an inert carrier and as an active ingredient, a plant growth regulatory effective or a herbicidally effective amount of a substantially pure triazolyl alcohol derivative represented by the general formula:

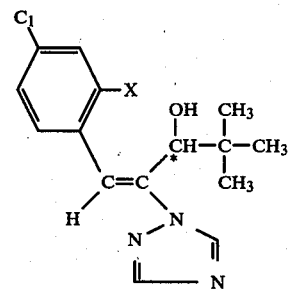

wherein X represents a hydrogen atom or a chlorine atom and the asterisk indicates an asymmetric carbon atom and having an optical activity of (+).

8. A method for killing a fungus, which comprises applying a fungicidal composition according to claim 6 to the fungus.

9. A method for controlling plant growth, which comprises applying a plant growth regulatory composition according to claim 7 to the plant.

10. A method for killing weed, which comprises applying a herbicidal composition according to claim 7 to the weed.

* * * * *